United States Patent
Ma et al.

(10) Patent No.: US 8,449,593 B2
(45) Date of Patent: May 28, 2013

(54) STENT AND STENT DELIVERY SYSTEM FOR SIDE-BRANCH LOCATIONS IN A CONDUIT

(75) Inventors: Jianlu Ma, Maple Grove, MN (US); Joe Tatalovich, St. Louis Park, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/466,552

(22) Filed: May 8, 2012

(65) Prior Publication Data

US 2012/0245673 A1    Sep. 27, 2012

Related U.S. Application Data

(63) Continuation of application No. 11/935,008, filed on Nov. 5, 2007, now abandoned.

(60) Provisional application No. 60/864,235, filed on Nov. 3, 2006.

(51) Int. Cl.
*A61F 2/06* (2006.01)

(52) U.S. Cl.
USPC .......................................................... 623/1.11

(58) Field of Classification Search
USPC .......................................................... 623/1.31
See application file for complete search history.

(56) References Cited

U.S. PATENT DOCUMENTS

| | | | |
|---|---|---|---|
| 5,607,444 | A | 3/1997 | Lam |
| 5,632,762 | A | 5/1997 | Myler |
| 5,749,890 | A | 5/1998 | Shaknovich |
| 5,868,777 | A | 2/1999 | Lam |
| 6,096,071 | A | 8/2000 | Yadav |
| 2004/0254627 | A1 | 12/2004 | Thompson et al. |
| 2007/0179590 | A1 | 8/2007 | Lu et al. |

*Primary Examiner* — Melanie Tyson
(74) *Attorney, Agent, or Firm* — Alana T. Bergman, Esq.

(57) ABSTRACT

A method for the placement of medical devices within a body lumen defined by a vessel wall is disclosed. The method includes the steps of providing a first and second medical device each having a tubular body with a plurality of slits extending through the side wall to form a plurality of sidewall segments, disposing the first medical device within the body lumen . . . initiating radial expansion of the second medical device such that flared second wall segments at least partially cover the slits of the first medical device. Medical devices and a system of medical devices capable of performing the method are also disclosed.

6 Claims, 7 Drawing Sheets

STENT AND STENT DELIVERY SYSTEM FOR SIDE-BRANCH LOCATIONS IN A CONDUIT

CROSS REFERENCE TO RELATED APPLICATIONS

This application is a Continuation Application of U.S. patent application Ser. No. 11/935,008, which was filed on Nov. 5, 2007 and which claims priority to U.S. Provisional Application 60/864,235, which was filed on Nov. 3, 2006, each of which is expressly incorporated herein by reference in its entirety.

FIELD OF THE INVENTION

The present invention relates to luminal implants, and, more particularly, to stents for use in treating vascular disease.

BACKGROUND OF THE INVENTION

Stents are widely used for supporting a lumen structure in a patient's body. For example, a stent may be used to maintain patency of a coronary artery, other blood vessel or other body lumen such as the ureter, urethra, bronchus, esophagus, or other passage. A stent is typically a metal, tubular structure, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs.

In certain stent designs, the stent is an open-celled tube that is expanded by an inflatable balloon at the deployment site. Another type of stent is of a "self-expanding" type. A self-expanding stent does not use a balloon or other source of force to move from a collapsed state to an expanded state. A self-expanding stent is passed through the body lumen in a collapsed state. At the point of an obstruction, or other deployment site in the body lumen, the stent is expanded to its expanded diameter for its intended purpose. An example of a self-expanding stent is a coil structure that is secured to a stent delivery device under tension in a collapsed state. At the deployment site, the coil is released so that the coil can expand to its enlarged diameter. Coil stents can be manufactured using a variety of methods, such as winding of wire, ribbon, or sheet on a mandrel or by laser cutting from a tube, followed by the appropriate heat treatments. Another type of self expanding stent is an open-celled tube made from a self-expanding material, for example, the Protégé GPS stent from ev3, Inc. of Plymouth, Minn. Open cell tube stents are commonly made by laser cutting of tubes, or cutting patterns into sheets followed by or preceded by welding the sheet into a tube shape, and other methods.

The shape, length and other characteristics of a stent are typically chosen based on the location in which the stent will be deployed. However, selected segments of the human vasculature present specific challenges due to their shape and configuration. One such situation involves the ostium of short renal arteries within the human body.

Conventional stents are generally designed for segments of long cylindrical vessels. When such stents are deployed at the ostium of short renal arteries, in an attempt to prevent further progression of arteriosclerotic disease from the aorta into the renal arteries, they may extend into the aorta and disrupt the normally laminar blood flow. This result further compounds an existing need to minimize disruption of the flow pattern at the ostium. In addition, stents are hard to position on a consistent basis at the precise ostial location desired, and placement of renal stents can release arteriosclerotic debris from the treatment area. Such debris can flow distally into the kidney and embolize, causing impaired renal function.

Accordingly, it is desirable to flare the end of a stent to minimize disruption to flow patterns at an ostium and to not create barriers to future access by interventional devices. However, existing stents are hard to flare with existing expansion means. Stents suitable for expansion of renal arteries must have high radial strength when expanded to resist vessel forces tending to radially collapse the stent. This need for high stent strength makes suitable stents difficult to flare at the ostium. A stent configuration designed to address these concerns is disclosed in commonly assigned U.S. patent application Ser. No. 10/816, 784, filed Apr. 2, 2004, by Paul J. Thompson and Roy K. Greenberg, US Publication Number U.S. 2004/0254627 A1. However, this stent, when flared, has a lower percentage of stent strut coverage of vessel wall at flared regions than is desirable. It is known that stent struts, when expanded into contact with the vessel wall, should cover a certain percentage of the internal vessel wall area in order to prevent prolapse of tissue through the open spaces between stent struts.

Accordingly, a need exists for a stent that can be placed at the renal ostium which is both strong and provides a high percentage of vessel wall coverage.

Further need exists for a stent that will minimize disruption of the flow pattern at the ostium and which will lower the risk of embolization during deployment.

SUMMARY OF THE INVENTION

A renal stent comprises a substantially cylindrical segment which is deployed in the renal vessel and a flared segment which is deployed in ostial and aortic regions of the vessel. The substantially cylindrical segment provides superior radial strength for maintaining dilated diameter of the renal vessel. The flared segment, which is formed by a plurality of slits extending through the sidewall of the stent, expands to conform to the ostial and aortic regions of the vessel. The flared segment can be balloon dilated to enhance conformance of the flared stented segment to the ostial and aortic regions. A stent delivery system capable of delivering and deploying the substantially cylindrical segment and the flared segment is also provided.

According to a first aspect of the disclosure, a medical device for insertion into a body lumen comprises a tubular body having a length extending along an axis between first and second ends thereof. The tubular body has a sidewall with a plurality of slits extending therethrough from the first end toward the second end. The plurality of slits extend less than the length of the tubular body and define a plurality of sidewall segments having different radial expansion characteristics, relative to the axis, than non-slitted portions of the tubular body. A plurality of radiopaque markers are disposed at the second end of the tubular body and have a defined relationship to the number and position of the plurality of slits.

According to a second aspect of the disclosure, a medical device for insertion into a body vessel comprises a first tubular section having a length extending along an axis between first and second ends thereof. The first tubular section has a sidewall with a plurality of slits extending through the sidewall for less than the length thereof from the first end toward the second end. A second tubular section extends along the axis and is also radially expandable. A mechanism joins the second end of the first tubular section, proximal of said plurality of slits, to the second tubular section. The first tubular section has different radial expansion characteristics, relative to the axis, than the second tubular section. In one embodiment, the first tubular section is self expanding while the second tubular section may be balloon expandable.

According to a third aspect of the disclosure, a method for placement of a medical device within a body lumen defined by a vessel wall comprises: (a) disposing a first tubular medical device within the body lumen, the first medical device having a tubular body extending along an axis and a plurality of slits extending through a sidewall thereof to form a plurality of first sidewall segments; (b) initiating radial expansion of the first medical device so that a first end thereof forms an alternating pattern of flared first sidewall segments and slits disposed adjacent the vessel wall; (c) disposing a second tubular medical device coaxially within the within first tubular medical device, the second medical device having a tubular body extending along said axis and having a plurality of slits extending through a sidewall thereof to form a plurality of second sidewall segments; and (d) initiating radial expansion of the second medical device so that a first end thereof forms an alternating pattern of flared second sidewall segments and slits, the first and second medical devices coaxially and rotationally aligned so that the flared second sidewall segments of the second medical device at least partially cover the slits of the first tubular medical device.

According to a fourth aspect of the disclosure, a method for placement of a medical device within a body lumen defined by a vessel wall comprises: (a) providing first and second medical devices, each medical device having a tubular body extending along an axis between first and second ends thereof, and a sidewall with a plurality of slits extending through the sidewall thereof to form a plurality of sidewall segments; (b) disposing the first medical device within the body lumen so that the first end thereof is disposed within an ostium of the body lumen; (c) initiating radial expansion of at least the first end of the first medical device to form an alternating pattern of flared first sidewall segments and slits disposed adjacent the vessel wall; (d) disposing the second medical device coaxially within the first medical device so that the first end thereof is disposed within an ostium of the body lumen; and (e) initiating radial expansion of the second medical device so that a first end thereof forms an alternating pattern of flared second sidewall segments and slits, the first and second medical devices disposed with the body lumen and rotationally aligned so that the flared second sidewall segments of the second medical device at least partially cover the slits of the first tubular medical device.

BRIEF DESCRIPTION OF THE DRAWINGS

The above and further advantages of the invention may be better understood by referring to the following description in conjunction with the accompanying drawings in which.

DETAILED DESCRIPTION

Figure 1:
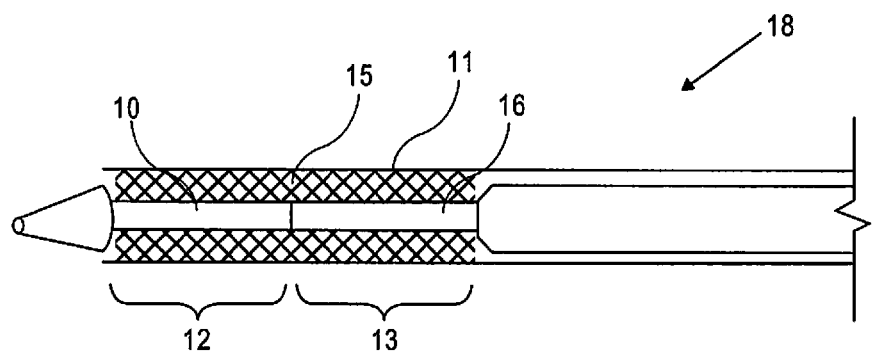
FIGS. 1-4 illustrate conceptually a partial cross-sectional diagram of a stent and a plan view of a stent delivery system in accordance with the present disclosure.

FIG. 1 illustrates a stent 15 in accordance with the present disclosure. Stent 15 comprises a substantially cylindrical stent segment 12 and a flared stent segment 13. Substantially cylindrical stent segment 12 may be balloon expandable and may comprise stainless steel alloys, cobalt chrome alloys, titanium, tantalum, platinum, gold, or other materials or their alloys as are known in the art. Flared stent segment 13 may be self expanding and may be comprise high elastic limit materials such as Elgiloy, cobalt chrome alloys, engineering polymers such as polyimide, PEEK (polyetheretherketone), polycarbonate, liquid crystal polymer, polyester, or other materials as are known in the art. The flared stent segment 13 may comprise so-called superelastic or shape-memory metals such as nitinol. Shape-memory metal stents can self-expand when thermo mechanically processed to exhibit superelastic material properties. Such shape-memory stents can also self-expand through use of a pre-programmed shape memory effect. Stents processed to exhibit a shape memory effect experience a phase change at or near the elevated temperature of the human body. The phase change results in expansion of the stent from a collapsed state to an enlarged state.

Figure 2:
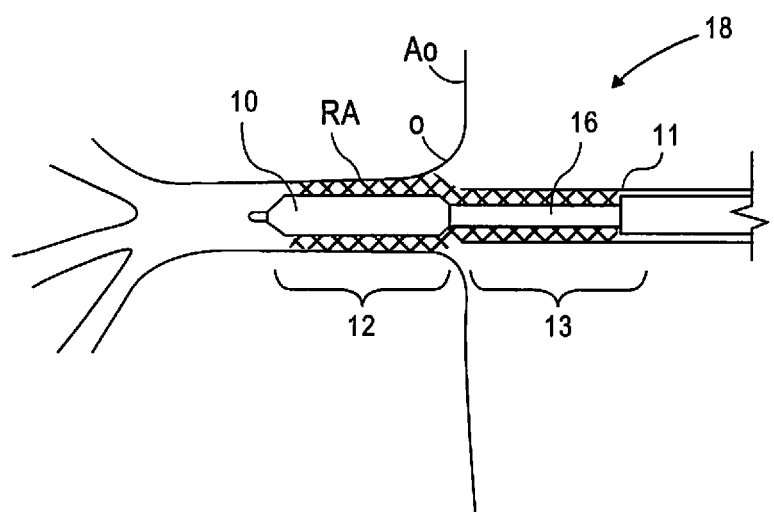
Figure 3:
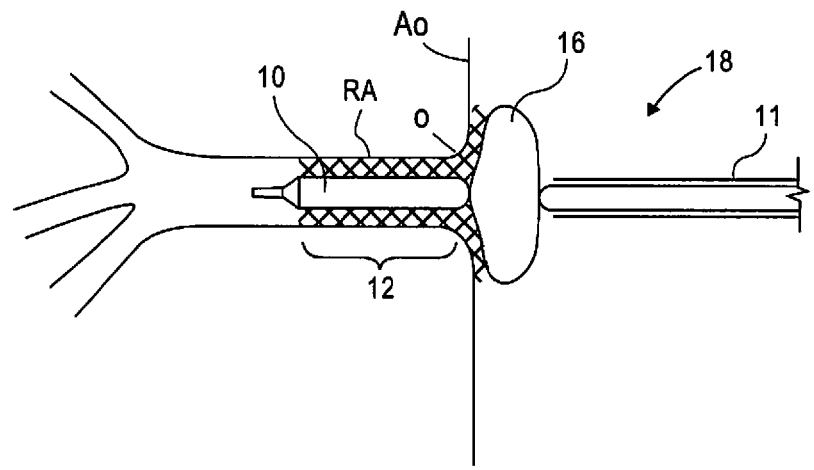
Figure 4:
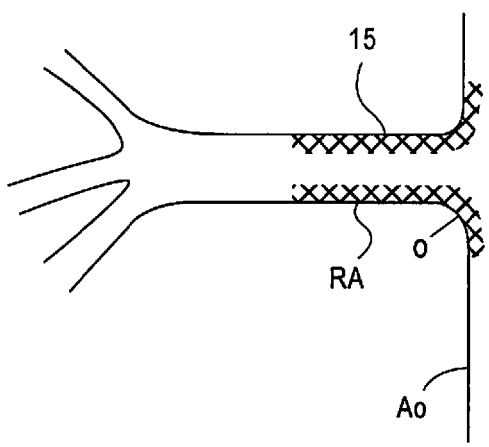

FIGS. 1-4 show delivery of inventive stent 15 to a treatment site. In use, stent 15 is delivered to the treatment site, typically a renal artery, on catheter 18 with an outer sheath 11 coaxially retractable from inner balloons 10, 16, as illustrated in FIG. 1. Outer sheath 11 constrains at least the flared segment 13 of stent 15. Distal balloon 10 is used to expand substantially cylindrical segment 12 of stent 15. Optional proximal balloon 16 may be used to dilate flared segment 13 of stent 15. At the treatment site, distal balloon 10 is inflated to expand substantially cylindrical segment 12 and dilate artery RA, thereby securing the stent at the treatment site, as illustrated in FIG. 2. Outer sheath 11 is then withdrawn, preferably before deflation of distal balloon 10, and flared segment 13 is diametrically enlarged to conform to the (typically) flared ostial O and/or aortic Ao regions near the vessel, as illustrated in FIG. 3. In some embodiments, flared segment 13 of stent 15, that is the portion of the stent 15 opposite the ostial O and aortic Ao regions, can be further dilated with proximal balloon 16. Inflated distal balloon 10 helps to axially anchor catheter 18 in vessel RA so that proximal balloon 16 can deliver force to flared stent segment 13 and thereby enhance stent segment 13 apposition to ostial and aortic regions of the vessel. Balloons 10 and 16 are then deflated. Optionally outer sheath 11 is advanced relative to balloons 10 and 16 to cover the balloons in whole or in part, and stent delivery catheter 18 is withdrawn from the treatment site, as illustrated in FIG. 4. It is not necessary to position substantially cylindrical stent segment 12 in vessel RA with precision because subsequent expansion of the flared stent segment 13 will assure continuous coverage of the vessel wall in regions RA, O, and Ao. Stenting of the vessel RA, ostium O, and aorta Ao is accomplished by delivery of one stent to the region thereby reducing the amount of debris generated during stenting as compared to procedures involving delivery of multiple devices.

Figure 5A:
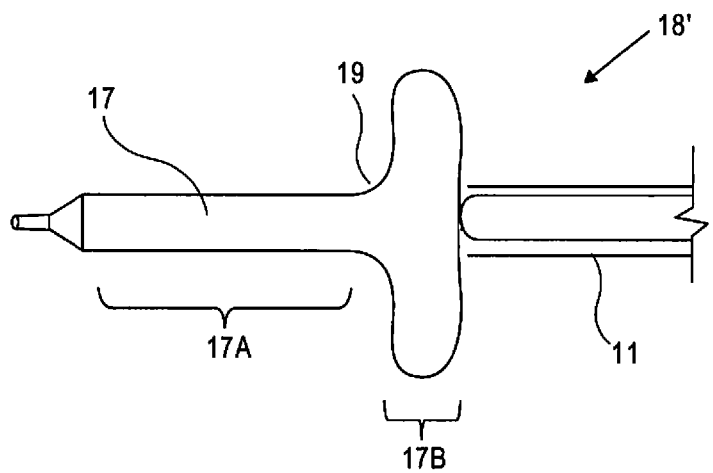
FIGS. 5A and 5B illustrate conceptually alternate embodiments of the delivery system of FIGS. 1-4.
Figure 5B:
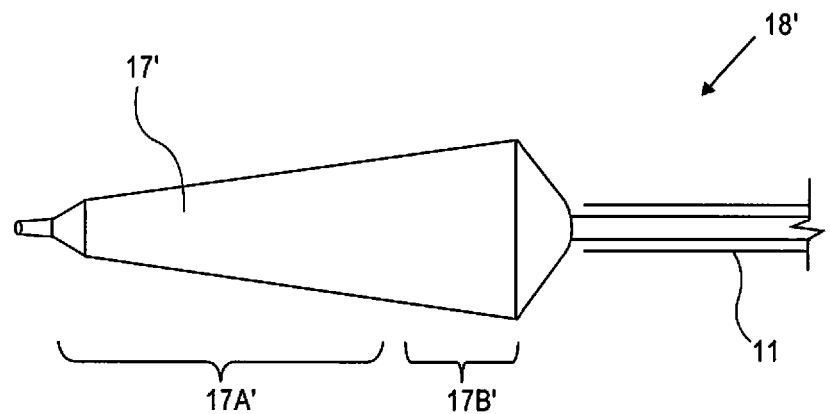

FIGS. 5A and 5B show alternative embodiments of a delivery system 18' similar in most respects to the delivery system 18 shown in FIGS. 1-4. In most respects the delivery system shown in FIG. 5 is used in a manner similar to that described above in conjunction with FIGS. 1-4. In these embodiments, balloons 17, 17' provide the function of both balloons 10 and 16 of delivery system 18. With sheath 11 covering flared stent segment 13 and balloon portion 17b, 17b', balloon portion 17a, 17a' is used to dilate substantially cylindrical stent segment 12. Subsequently, balloon 17, 17' is deflated to a pressure low enough to allow proximal withdrawal of sheath 11 until it no longer covers flared stent segment 13 and balloon portion 17b, 17b'. Next, balloon 17, 17' is inflated, causing balloon portion 17a, 17a' to anchor catheter 18' in the vessel and causing balloon portion 17b, 17b' to further dilate flared stent portion 13. In this embodiment, balloon 17, 17' may be constructed from appropriate materials so as to have differing compliance characteristics between sections 17a, 17a' and 17b, 17b' at the same inflation pressure, or, balloon 17, 17' may be formed to assume a profile similar to that illustrated in FIGS. 5A, 5B, or another profile. FIGS. 5A and 5B illustrate balloons having an enlarged diameter proximal portion 17b, 17b' as compared to diameter of distal portion 17a, 17a'. In FIG. 5A an abrupt change in balloon diameter 19 divides proximal portion 17b from distal portion 17a. In FIG. 5B gradual change in balloon diameter divides proximal portion 17b' from distal portion 17a'. In other embodiments two or more balloons can be attached to one catheter shaft to provide the above described functions of balloons 17, 17'.

Figure 6A:
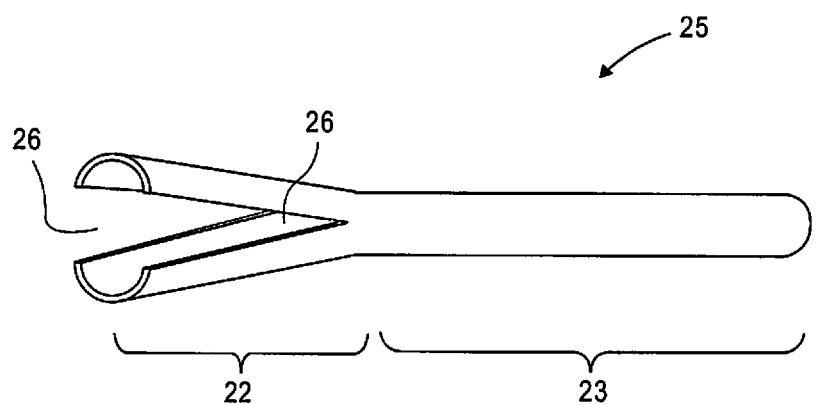
FIGS. 6A-6F illustrate conceptually isometric or side view diagrams of other embodiments of stents in accordance with the present disclosure.
Figure 6B:
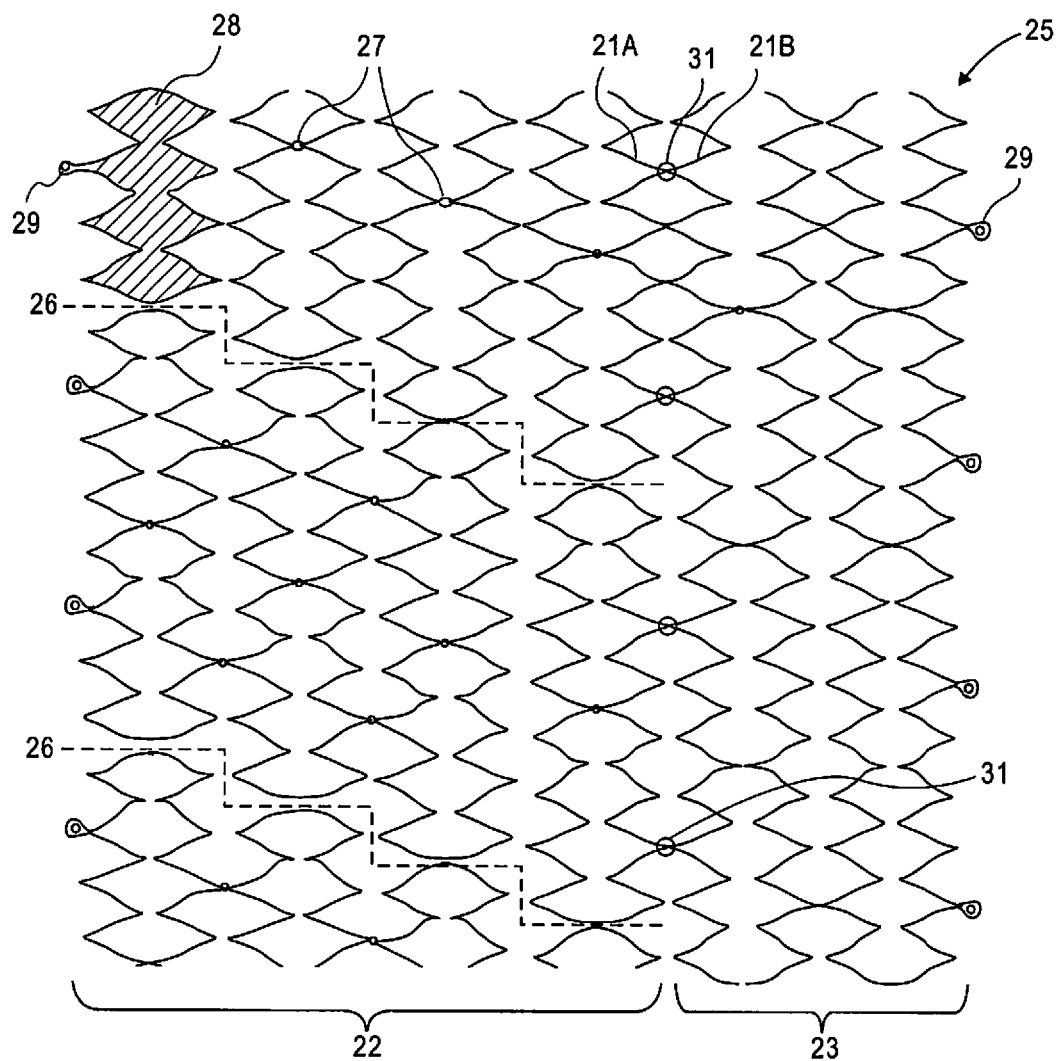

FIGS. 6A and 6B illustrate another embodiment of a stent 25 in accordance with the present disclosure. Stent 25 comprises a substantially cylindrical stent segment 23 and a flared stent segment 22. Substantially cylindrical stent segment 23 and flared stent segment 22 may be balloon expandable and may comprise stainless steel alloys, cobalt chrome alloys, titanium, tantalum, platinum, gold, engineering polymers such as polyimide, PEEK (polyetheretherketone), polycarbonate, liquid crystal polymer, polyester, or other materials or their alloys as are known in the art. In another embodiment substantially cylindrical stent segment 23 and flared stent segment 22 may be self expanding and may be comprise high elastic limit materials such as Elgiloy, cobalt chrome alloys, engineering polymers such as polyimide, PEEK (polyetheretherketone), polycarbonate, liquid crystal polymer, polyester, or other materials as are known in the art. The self expanding stent segments 22, 23 may comprise so-called superelastic or shape-memory metals such as nitinol. Shape-memory metal stents can self-expand when thermo mechanically processed to exhibit superelastic material properties. Such shape-memory stents can also self-expand through use of a pre-programmed shape memory effect. Stents processed to exhibit a shape memory effect experience a phase change at the elevated temperature of the human body. The phase change results in expansion of the stent from a collapsed state to an enlarged state. Self expanding stent segments, in some embodiments, are heat set to a substantially cylindrical expanded shape, and in other embodiments, are shape set into a flared expanded shape.

Flared segment of stent 25 is shown partially expanded in FIG. 6A and comprises slits 26 in sidewall of stent. In one embodiment stent 25 has two slits disposed about the perimeter of the tubular body defined by the stent sidewall. In another embodiment, stent 25 has three slits, in another embodiment stent 25 has four slits, in another embodiment stent 25 has 5 or 6 slits, in another embodiment stent 25 has 7-10 slits, and in another embodiment stent 25 has more than 10 slits. Slits 26 may be equally spaced around perimeter of stent 25 or may be unequally spaced around perimeter of stent 25. In one embodiment, shown in FIG. 6B, stent 25 comprises a laser cut tube having struts 21a, 21b and radially expandable cells 28 joined at attachment points 27. A line drawn through attachment points 27 on the surface of the cylindrical stent will traverse a helical path. Such an arrangement enables the stent to have good axial and bending properties. Slit 26 is represented by dashed lines in FIG. 6B and forms breaks or discontinuities in the pattern of cells 28. Stent 25 may also comprise one or more radiopaque markers 29 as are known in the art which facilitate fluoroscopic placement of the stent within the body. In one embodiment, the radiopaque markers 29 may be located on the proximal or non-flared end of the stent 25 with the number and position of the radiopaque markers 29 about the perimeter of the stent sidewall having a defined correspondence to the position and number of either the flared segments 22 or slits 26. For clarity, stent 25 is shown cut along its axial length and laid flat in FIG. 6B. Also, in FIG. 6B, cylindrical segment 23 is illustrated as shorter than flared segment 22, however, cylindrical segment 23 may be longer than flared segment 22 or the two segments may have the same length. Manufacturing methods other than laser cutting may be used to make stent 25, including but not limited to chemical etching, grinding, machining, molding, thermoforming, casting, and other methods.

Figure 6C:
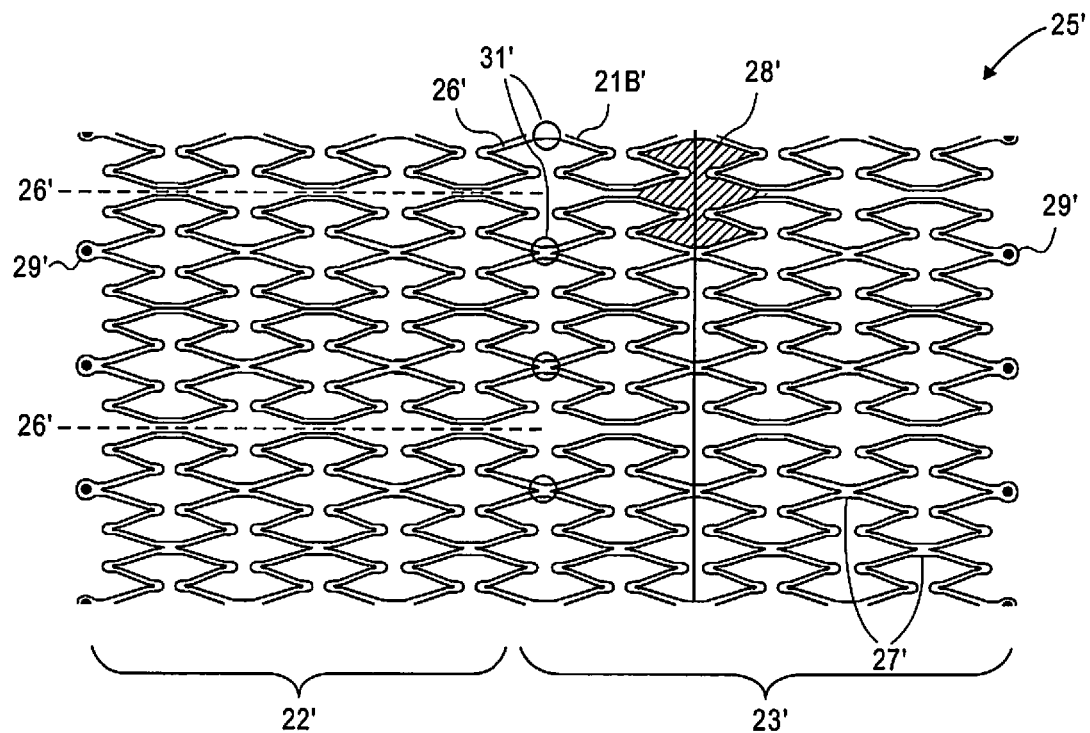

In another embodiment, a stent 25' is shown in FIG. 6C and comprises slits 26' in sidewall of stent. In one embodiment stent 25' has two slits, in another embodiment stent 25' has three slits, in another embodiment stent 25' has four slits, in another embodiment stent 25' has 5 or 6 slits, in another embodiment stent 25' has 7-10 slits, and in another embodiment stent 25' has more than 10 slits. Slits 26' may be equally spaced around perimeter of stent 25' or may be unequally spaced around perimeter of stent 25'. In one embodiment, shown in FIG. 6C, stent 25' comprises a laser cut tube having struts 21a', 21b' and radially expandable cells 28' joined at attachment points 27'. A line drawn through attachment points 27' on the surface of the cylindrical stent will traverse a straight path. Such an arrangement enables the stent to have stiff axial and bending properties. Slit 26' is represented by dashed lines in FIG. 6C. Stent 25' may also comprise one or more radiopaque markers 29' as are known in the art. For clarity, stent 25' is shown cut along its axial length and laid flat in FIG. 6C. Also, in FIG. 6C, cylindrical segment 23' and flared segment 22' are illustrated as being similar in length, however, cylindrical segment 23' may be longer or shorter than flared segment 22. Manufacturing methods other than laser cutting may be used to make stent 25', including but not limited to chemical etching, grinding, machining, molding, thermoforming, casting, and other methods.

Figure 6F:
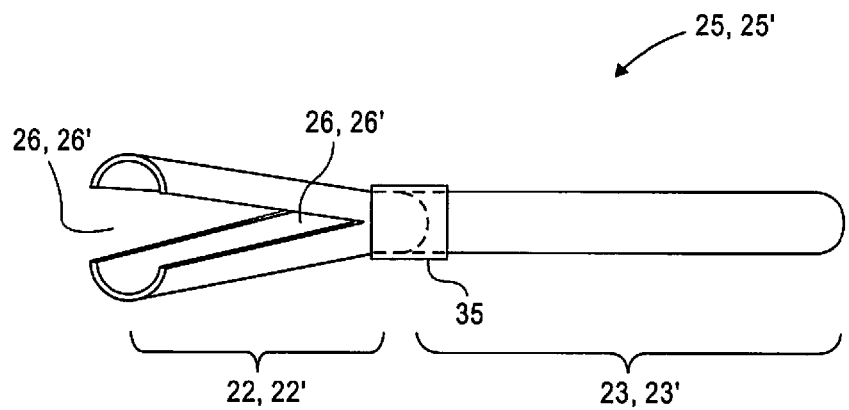
Figure 6D:
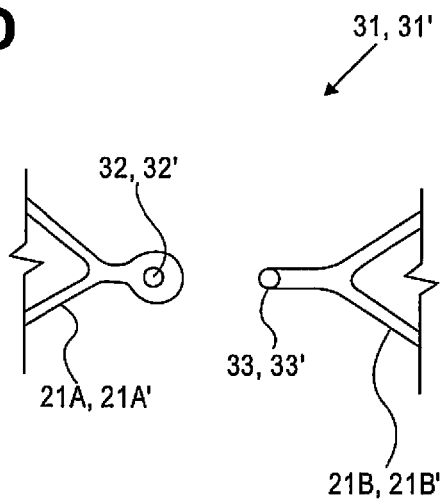
Figure 6E:
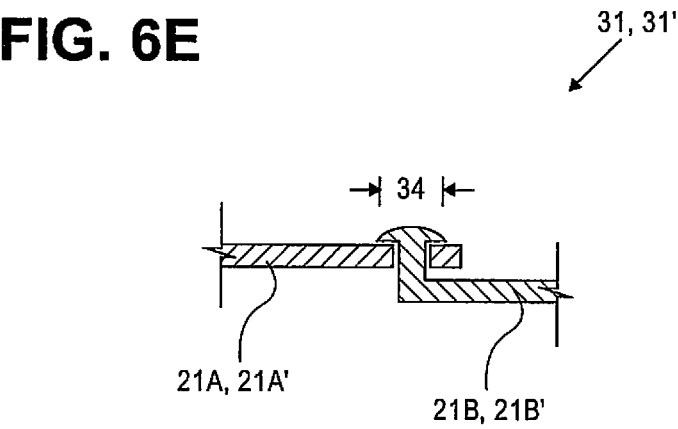

In another embodiment stent 25, 25' comprise a cylindrical segment 23, 23' and a flared segment 22, 22', joined at attachment sites 31, 31' as illustrated in FIGS. 6D (partial plan view of unassembled attachment site) and 6E (cross-sectional view of assembled attachment site). In one embodiment cylindrical segment 23, 23' is metallic and flared segment 22, 22' is polymeric, in another embodiment cylindrical segment 23, 23' is polymeric and flared segment 22, 22' is metallic. Attachment sites 31, 31' comprise strut 21a, 21a' having opening 32, 32' and strut 21b, 21b' having pin 33, 33'. To attach cylindrical and flared segments, pin 33, 33' is inserted through opening 32, 32', respectively. The end of pin 33, 33" is enlarged to a diameter 34 larger than opening so as to prevent pin from exiting from opening.

Other attachment methods for stent segments 22, 22', 23, 23' will be apparent to those skilled in the art, such as welding, overmolding, thermoforming, bonding, and other methods. In one embodiment, illustrated in FIG. 6F, a cover 35 is used to join cylindrical segment 23, 23' to flared segment 22, 22'. In one embodiment, cover 35 is a thin cylinder of expanded polytetrafluoroethylene bonded to stent segments using a thin sheet of polyethylene as an adhesive layer between the stent segments and the cover. Other bonding methods will be apparent to those skilled in the art.

Figure 7:
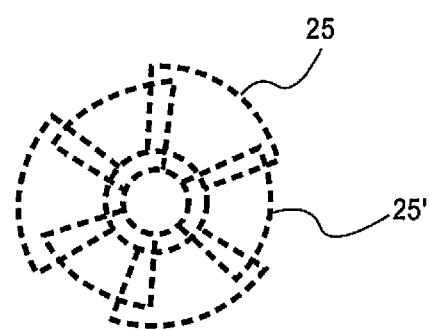
FIG. 7 is an end view conceptually illustrating the coaxial placement and alignment of stents in accordance with the present disclosure.

Stents 25 and 25' can be delivered to and deployed in the vicinity of a treatment site using methods similar to those described above for inventive stent 15 with reference to FIGS. 1-5. In one embodiment, two inventive stents 25 and 25', each having three slits, are implanted, one coaxial with the other, and rotationally oriented such that the slits of the inner stent align with cells of the outer stent, so as to provide partial or full stent strut coverage of the vessel wall in the ostial and aortic regions, as illustrated conceptually in the end view of FIG. 7. The process of placement of multiple stents, as described herein, may involve placement of the stent within the body lumen followed by and expansion or flaring of the sidewall segments against the vessel wall so that the flared ends of the stent are disposed within the vessel ostium. The another stent is then positioned coaxially within the previously position to stent and rotationally aligned therewith so that the flared sidewall segments of the second stent at least partially cover any exposed areas of the vessel wall. Depending on the number of stents nested in this matter, there may be varying degrees of overlap between the respective flared sidewall segments of the concentrically nested stents. The radiopaque markers described herein facilitate rotational alignment of stents during placement within the body lumen. Specifically, if the number and position of radiopaque markers has a defined relationship with each sidewall segment or slit, then a practitioner may position and rotationally align two or more stents by fluoroscopically detecting the pattern of radiopaque markers for each stent and rotationally aligning the same so that the radiopaque markers of different stents are interleaved. Such practice provides a fluoroscopically detectable approximation of the position of the slits and wall segments and facilitates overlap positioning of the flared wall segments against the vessel wall in the ostium region in a manner that provides maximum vessel wall coverage, as illustrated in FIG. 7. In another embodiment, three inventive stents 25, 25' and 25" each having two or more slits, are implanted, each coaxial with the others, and rotationally oriented such that the slits of the three stents align in such a way as to provide partial or full stent strut coverage of the vessel wall in the ostial and aortic is regions, in a manner similar to that illustrated conceptually in the end view of FIG. 7. Although the embodiment illustrated in FIG. 7 is shown using two stents, each having three slits, other inventive arrangements may be utilized in which two or more stents, each having two or more slits, may be aligned in various arrangements to provide partial or full stent strut coverage of the vessel wall in the ostial and aortic regions. In such inventive arrangements, the struts of different stents may provide overlapping coverage of the vessel wall in the ostial and aortic regions.

While this document has described a disclosure mainly in relation to renal artery stenting, it is envisioned that the disclosure can be applied to other conduits in the body as well including arteries, veins, bronchi, ducts, ureters, urethra, and other lumens intended for the passage of air, fluids, or solids. The disclosure can be applied to any site of branching of an artery, vein, bronchus, duct, ureter, urethra, and other lumen including but not limited to the junction of the common, internal, and external carotid arteries, the junction of the main, left anterior descending, and circumflex coronary arteries, the junction of the left main or right coronary artery with the aorta, the junction of the aorta with the subclavian artery, and the junction of the aorta with the carotid artery.

While the various embodiments of the present invention have related to stents and stent delivery systems, the scope of the present invention is not so limited. Further, while choices for materials and configurations may have been described above with respect to certain embodiments, one of ordinary skill in the art will understand that the materials described and configurations are applicable across the embodiments.

What is claimed is:

1. A method for placement of medical devices within a body lumen defined by a vessel wall comprising:
   disposing a first tubular medical device within the body lumen, the first medical device having a tubular body extending along an axis and a plurality of slits extending through a sidewall thereof to form a plurality of first sidewall segments;
   initiating radial expansion of the first medical device so that a first end thereof forms an alternating pattern of flared first sidewall segments and slits disposed adjacent the vessel wall;
   disposing a second tubular medical device coaxially within the first tubular medical device, the second medical device having a tubular body extending along said axis and having a plurality of slits extending through a sidewall thereof to form a plurality of second sidewall segments; and
   initiating radial expansion of the second medical device so that a first end thereof forms an alternating pattern of flared second sidewall segments and slits,
   the first and second medical devices coaxially and rotationally aligned so that the flared second sidewall segments of the second medical device at least partially cover the slits of the first tubular medical device.

2. The method of claim 1 wherein the first and second medical devices each further comprise a plurality of radiopaque markers disposed at respective second ends thereof, the plurality of radiopaque markers of each medical device having a defined relationship to the number and position of the plurality of slits in their respective tubular bodies.

3. A method for placement of medical devices within a body lumen defined by a vessel wall comprising:
   providing first and second medical devices, each medical device having a tubular body extending along an axis between first and second ends thereof, and a sidewall with a plurality of slits extending through the sidewall thereof to form a plurality of sidewall segments;
   disposing the first medical device within the body lumen so that the first end thereof is disposed within an ostium of the body lumen;
   initiating radial expansion of at least the first end of the first medical device to form an alternating pattern of flared first sidewall segments and slits disposed adjacent the vessel wall;
   disposing the second medical device coaxially within the first medical device so that the first end thereof is disposed within an ostium of the body lumen; and
   initiating radial expansion of the second medical device so that a first end thereof forms an alternating pattern of flared second sidewall segments and slits,
   the first and second medical devices disposed with the body lumen and rotationally aligned so that the flared second sidewall segments of the second medical device at least partially cover the slits of the first tubular medical device.

4. The method of claim 3 wherein the first and second medical devices are disposed with the body lumen and rotationally aligned about their respective axes so that the flared second sidewall segments of the second medical device substantially cover the slits of the first tubular medical device.

5. The method of claim 3 wherein the first and second medical devices are disposed with the body lumen and rotationally aligned about their respective axes so that the flared second sidewall segments of the second medical device at least partially cover the flared first sidewall segments of the first medical.

6. The method of claim 3 wherein the first and second medical devices each further comprise a plurality of radiopaque markers disposed at respective second ends thereof, the plurality of radiopaque markers of each medical device having a defined relationship to the number and position of the plurality of slits in their respective tubular bodies.

\* \* \* \* \*